US012576262B2

(12) United States Patent
Edwards et al.

(10) Patent No.: US 12,576,262 B2
(45) Date of Patent: Mar. 17, 2026

(54) MAGNETIC PROPULSION AND BEARING FOR A HEMODYNAMIC SUPPORT PUMP

(71) Applicant: Boston Scientific Scimed Inc., Maple Grove, MN (US)

(72) Inventors: Nathan Edwards, Minneapolis, MN (US); Steven R. Larsen, Lino Lake, MN (US); Travis J. Schauer, Rockford, MN (US); Jeffrey Lucas, Hopkins, MN (US); Lloyd Radman, Blaine, MN (US); Sam Murthy, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 900 days.

(21) Appl. No.: 17/669,163

(22) Filed: Feb. 10, 2022

(65) Prior Publication Data

US 2022/0249829 A1 Aug. 11, 2022

Related U.S. Application Data

(60) Provisional application No. 63/147,998, filed on Feb. 10, 2021.

(51) Int. Cl.
A61M 60/82 (2021.01)
A61M 60/13 (2021.01)
(Continued)

(52) U.S. Cl.
CPC ............ A61M 60/82 (2021.01); A61M 60/13 (2021.01); A61M 60/148 (2021.01);
(Continued)

(58) Field of Classification Search
CPC .. F04D 29/048; F04D 13/024; F04D 13/0633; F16C 2316/18; A61M 60/419;
(Continued)

(56) References Cited

U.S. PATENT DOCUMENTS 5,145,333 A 9/1992 Smith
5,211,546 A 5/1993 Isaacson et al.
(Continued)

FOREIGN PATENT DOCUMENTS

DE 3338002 A1 5/1985
EP 0847767 A1 6/1998
(Continued)

OTHER PUBLICATIONS

US 9,067,007 B2, 06/2015, Tanner et al. (withdrawn)
(Continued)

*Primary Examiner* — Peter J Bertheaud
(74) *Attorney, Agent, or Firm* — Seager, Tufte & Wickhem LLP

(57) ABSTRACT

Various aspects of the present disclosure are directed towards apparatuses, systems, and methods that may include a blood pump. The blood pump may include a magnetic field source and an impeller assembly. The impeller assembly includes an impeller and a driven magnet. The driven magnet is longitudinally offset and distally disposed relative to the magnetic field source, and the driven magnet is rotatable and longitudinally controlled by the magnetic field source. The driven magnet includes a distal side, the distal side faces the impeller. The blood pump further includes a bearing assembly near the distal side of the driven magnet.

10 Claims, 10 Drawing Sheets

(51) Int. Cl.

| | |
|---|---|
| *A61M 60/148* | (2021.01) |
| *A61M 60/216* | (2021.01) |
| *A61M 60/221* | (2021.01) |
| *A61M 60/419* | (2021.01) |
| *A61M 60/422* | (2021.01) |
| *A61M 60/492* | (2021.01) |
| *A61M 60/804* | (2021.01) |
| *A61M 60/825* | (2021.01) |
| *F04D 13/02* | (2006.01) |
| *F04D 13/06* | (2006.01) |
| *F04D 29/048* | (2006.01) |

(52) U.S. Cl.
CPC ........ *A61M 60/216* (2021.01); *A61M 60/221* (2021.01); *A61M 60/419* (2021.01); *A61M 60/422* (2021.01); *A61M 60/492* (2021.01); *A61M 60/804* (2021.01); *A61M 60/825* (2021.01); *F04D 13/024* (2013.01); *F04D 13/0633* (2013.01); *F04D 29/048* (2013.01); *F16C 2316/18* (2013.01)

(58) Field of Classification Search
CPC .............. A61M 60/422; A61M 60/148; A61M 60/825; A61M 60/13; A61M 60/237; A61M 60/216; A61M 60/221; A61M 60/82
See application file for complete search history.

(56) References Cited

U.S. PATENT DOCUMENTS

| | | | |
|---|---|---|---|
| 5,507,629 | A | 4/1996 | Jarvik |
| 5,527,159 | A | 6/1996 | Bozeman, Jr. et al. |
| 5,611,679 | A | 3/1997 | Ghosh et al. |
| 5,692,882 | A | 12/1997 | Bozeman, Jr. et al. |
| 5,928,131 | A | 7/1999 | Prem |
| 5,947,703 | A | 9/1999 | Nojiri et al. |
| 5,947,892 | A | 9/1999 | Benkowski et al. |
| 5,964,694 | A | 10/1999 | Siess et al. |
| 6,135,729 | A | 10/2000 | Aber |
| 6,139,487 | A | 10/2000 | Siess |
| 6,155,969 | A * | 12/2000 | Schima ................ A61M 60/113 600/16 |
| 6,176,822 | B1 | 1/2001 | Nix et al. |
| 6,176,848 | B1 | 1/2001 | Rau et al. |
| 6,201,329 | B1 | 3/2001 | Chen |
| 6,227,820 | B1 | 5/2001 | Jarvik |
| 6,264,635 | B1 | 7/2001 | Wampler et al. |
| 6,447,266 | B2 | 9/2002 | Antaki et al. |
| 7,841,976 | B2 | 11/2010 | McBride et al. |
| 7,927,068 | B2 | 4/2011 | McBride et al. |
| 7,972,122 | B2 | 7/2011 | Larose et al. |
| 8,007,254 | B2 | 8/2011 | Larose et al. |
| 8,043,074 | B2 | 10/2011 | Tada |
| 8,376,707 | B2 | 2/2013 | McBride et al. |
| 8,512,012 | B2 | 8/2013 | Akdis et al. |
| 8,591,393 | B2 | 11/2013 | Walters et al. |
| 8,597,170 | B2 | 12/2013 | Walters et al. |
| 8,684,904 | B2 | 4/2014 | Campbell et al. |
| 8,721,517 | B2 | 5/2014 | Zeng et al. |
| 8,770,945 | B2 | 7/2014 | Ozaki et al. |
| 8,827,661 | B2 | 9/2014 | Mori |
| 8,992,163 | B2 | 3/2015 | McBride et al. |
| 9,067,005 | B2 | 6/2015 | Ozaki et al. |
| 9,072,825 | B2 | 7/2015 | Pfeffer et al. |
| 9,091,271 | B2 | 7/2015 | Bourque |
| 9,138,518 | B2 | 9/2015 | Campbell et al. |
| 9,162,017 | B2 | 10/2015 | Evans et al. |
| 9,199,020 | B2 | 12/2015 | Siess |
| 9,308,302 | B2 | 4/2016 | Zeng |
| 9,308,304 | B2 | 4/2016 | Peters et al. |
| 9,314,557 | B2 | 4/2016 | Ricci et al. |
| 9,327,067 | B2 | 5/2016 | Zeng et al. |
| 9,364,592 | B2 | 6/2016 | McBride et al. |
| 9,364,593 | B2 | 6/2016 | McBride et al. |
| 9,364,594 | B2 | 6/2016 | Nüsser et al. |
| 9,381,288 | B2 | 7/2016 | Schenck et al. |
| 9,421,311 | B2 | 8/2016 | Tanner et al. |
| 9,446,179 | B2 | 9/2016 | Keenan et al. |
| 9,616,157 | B2 * | 4/2017 | Akdis ................ F04D 29/0473 |
| 9,675,740 | B2 | 6/2017 | Zeng et al. |
| 9,717,833 | B2 | 8/2017 | McBride et al. |
| 9,770,543 | B2 | 9/2017 | Tanner et al. |
| 9,872,947 | B2 | 1/2018 | Keenan et al. |
| 9,895,476 | B2 | 2/2018 | Larose et al. |
| 9,907,890 | B2 | 3/2018 | Muller |
| 9,956,332 | B2 | 5/2018 | Larose et al. |
| 9,962,475 | B2 | 5/2018 | Campbell et al. |
| 9,964,115 | B2 | 5/2018 | Scheckel |
| 10,029,037 | B2 | 7/2018 | Muller et al. |
| 10,039,872 | B2 | 8/2018 | Zeng et al. |
| 10,071,192 | B2 | 9/2018 | Zeng |
| 10,086,121 | B2 | 10/2018 | Fitzgerald et al. |
| 10,105,475 | B2 | 10/2018 | Muller |
| 10,117,980 | B2 | 11/2018 | Keenan et al. |
| 10,149,932 | B2 | 12/2018 | McBride et al. |
| 10,215,187 | B2 | 2/2019 | McBride et al. |
| 10,232,099 | B2 | 3/2019 | Peters et al. |
| 10,251,985 | B2 | 4/2019 | Larose et al. |
| 10,251,986 | B2 | 4/2019 | Larose et al. |
| 10,478,539 | B2 | 11/2019 | Pfeffer et al. |
| 10,478,540 | B2 | 11/2019 | Scheckel et al. |
| 10,525,178 | B2 | 1/2020 | Zeng |
| 10,576,192 | B2 | 3/2020 | Muller et al. |
| 10,576,193 | B2 | 3/2020 | Tanner et al. |
| 10,704,553 | B2 | 7/2020 | Janeczek et al. |
| 10,709,829 | B2 | 7/2020 | Muller |
| 10,709,830 | B2 | 7/2020 | Tanner et al. |
| 10,765,789 | B2 | 9/2020 | Zeng et al. |
| 10,780,208 | B2 | 9/2020 | Siess et al. |
| 10,786,610 | B2 | 9/2020 | Zeng |
| 10,799,624 | B2 | 10/2020 | Pfeffer et al. |
| 10,842,921 | B2 | 11/2020 | Siess et al. |
| 10,864,308 | B2 | 12/2020 | Muller et al. |
| 10,864,309 | B2 | 12/2020 | McBride et al. |
| 10,874,783 | B2 | 12/2020 | Pfeffer et al. |
| 10,894,115 | B2 | 1/2021 | Pfeffer et al. |
| 10,918,774 | B2 | 2/2021 | Stanfield et al. |
| 10,960,116 | B2 | 3/2021 | Campbell et al. |
| 10,973,967 | B2 | 4/2021 | Nyikos et al. |
| 10,980,927 | B2 | 4/2021 | Pfeffer et al. |
| 11,058,865 | B2 | 7/2021 | Fitzgerald et al. |
| 11,097,092 | B2 | 8/2021 | Siess et al. |
| 11,107,626 | B2 | 8/2021 | Siess et al. |
| 11,123,539 | B2 | 9/2021 | Pfeffer et al. |
| 11,129,978 | B2 | 9/2021 | Pfeffer et al. |
| 11,167,124 | B2 | 11/2021 | Pfeffer et al. |
| 11,219,755 | B2 | 1/2022 | Siess et al. |
| 11,229,786 | B2 | 1/2022 | Zeng et al. |
| 11,235,138 | B2 | 2/2022 | Gross-Hardt et al. |
| 11,253,693 | B2 | 2/2022 | Pfeffer et al. |
| 11,260,213 | B2 | 3/2022 | Zeng et al. |
| 11,273,301 | B2 | 3/2022 | Pfeffer et al. |
| 11,311,712 | B2 | 4/2022 | Zeng et al. |
| 11,338,124 | B2 | 5/2022 | Pfeffer et al. |
| 11,357,967 | B2 | 6/2022 | Zeng et al. |
| 11,400,276 | B2 | 8/2022 | Chopra et al. |
| 11,471,664 | B2 | 10/2022 | Xu et al. |
| 11,497,896 | B2 | 11/2022 | Tanner et al. |
| 11,517,736 | B2 | 12/2022 | Earles et al. |
| 11,569,015 | B2 | 1/2023 | Mourran et al. |
| 11,583,659 | B2 | 2/2023 | Pfeffer et al. |
| 11,628,294 | B2 | 4/2023 | Chopra et al. |
| 11,648,388 | B2 | 5/2023 | Siess et al. |
| 11,672,968 | B2 | 6/2023 | Antaki |
| 11,708,833 | B2 | 7/2023 | McBride et al. |
| 11,754,075 | B2 | 9/2023 | Schuelke et al. |
| 11,786,700 | B2 | 10/2023 | Pfeffer et al. |
| 2002/0031436 | A1 | 3/2002 | Maeda et al. |
| 2008/0114339 | A1 | 5/2008 | McBride et al. |
| 2009/0060743 | A1 | 3/2009 | McBride et al. |
| 2011/0238172 | A1 | 9/2011 | Akdis |

(56)     References Cited

U.S. PATENT DOCUMENTS

| | | |
|---|---|---|
| 2017/0296725 A1 | 10/2017 | Peters et al. |
| 2018/0303990 A1 | 10/2018 | Siess et al. |
| 2018/0311423 A1 | 11/2018 | Zeng et al. |
| 2019/0275224 A1 | 9/2019 | Hanson et al. |
| 2020/0121835 A1 | 4/2020 | Farago et al. |
| 2020/0306434 A1 | 10/2020 | Vancamp et al. |
| 2021/0015982 A1 | 1/2021 | Kerkhoffs et al. |
| 2021/0023282 A1 | 1/2021 | Siess et al. |
| 2021/0038785 A1 | 2/2021 | Siess et al. |
| 2021/0069393 A1 | 3/2021 | Schauer et al. |
| 2021/0106810 A1 | 4/2021 | Pfeffer et al. |
| 2022/0134082 A1 | 5/2022 | Pfeffer et al. |
| 2022/0384070 A1 | 12/2022 | Mourran |
| 2023/0040593 A1 | 2/2023 | Liu et al. |

FOREIGN PATENT DOCUMENTS

| | | |
|---|---|---|
| EP | 2301598 A1 | 3/2011 |
| EP | 3069740 A1 | 9/2016 |
| EP | 3352808 B1 | 9/2023 |
| JP | 2001517102 A | 10/2001 |
| JP | 2002089491 A | 3/2002 |
| JP | 2018510708 A | 4/2018 |
| WO | 9500185 A1 | 1/1995 |
| WO | 9737698 A1 | 10/1997 |
| WO | 2016146661 A1 | 9/2016 |

OTHER PUBLICATIONS

International Search Report and Written Opinion for International Application No. PCT/US2022/016016, dated May 11, 2022. (10 pages).

* cited by examiner 132      107

MAGNETIC PROPULSION AND BEARING FOR A HEMODYNAMIC SUPPORT PUMP

CROSS-REFERENCE TO RELATED APPLICATION

This application claims priority to Provisional Application No. 63/147,998, filed Feb. 10, 2021, which is herein incorporated by reference in its entirety.

TECHNICAL FIELD

The present disclosure relates to percutaneous circulatory support devices. More specifically, the disclosure relates to bearing assemblies and magnetic driving systems for use in percutaneous circulatory support devices.

BACKGROUND

Percutaneous circulatory support devices such as blood pumps can provide transient support for hours or months of use in patients whose heart function or cardiac output is compromised. Magnetically driven pumps offer improvements over existing technologies as they offer easier therapeutic management, easier patient ambulation, and improved device durability. Wear at bearing surfaces can limit the lifetime of the devices and mechanical interactions with the blood at bearing surfaces can lead to hemolysis or other health complications. Blood contact with magnetic surfaces can also result in corrosion of components. Additionally, blood pump performance and blood flow rates may be impacted by component imbalance and insufficient magnetic torque generation and transfer between device components.

SUMMARY

In an Example 1, a blood pump comprises a magnetic field source; an impeller assembly including a longitudinal axis, an impeller, and a driven magnet, the driven magnet being longitudinally offset and distally disposed relative to the magnetic field source, the driven magnet being rotatable and longitudinally controlled by the magnetic field source, and the driven magnet comprising a distal side, the distal side facing the impeller; and a bearing assembly near the distal side of the driven magnet.

In an Example 2, the blood pump of Example 1, further comprising an impeller assembly housing, the bearing assembly being in contact with the impeller assembly housing, and the impeller assembly housing rotatably carrying the impeller assembly via the bearing assembly.

In an Example 3, the blood pump of Example 2, wherein the impeller assembly housing includes a recess that receives the bearing assembly.

In an Example 4, the blood pump of any of Examples 1-3, wherein the distance between the magnetic field source and the driven magnet is less than 0.030 inches.

In an Example 5, the blood pump of any of Examples 1-4, wherein the impeller assembly has a center of mass and the bearing assembly is aligned longitudinally with the center of mass of the impeller assembly.

In an Example 6, the blood pump of any of Examples 1-5, wherein no portion of the bearing assembly is located between the driven magnet and the magnetic field source.

In an Example 7, the blood pump of any of Examples 2-6, wherein the impeller assembly housing contains no bearing assembly located at a distal end of the impeller.

In an Example 8, the blood pump of any of Examples 1-7, wherein the impeller assembly is rotatable about the longitudinal axis, and the bearing assembly is disposed radially outwardly relative to the longitudinal axis.

In an Example 9, the blood pump of any of Examples 2-8, wherein the impeller assembly further includes a shaft, and the bearing assembly contacts the shaft and the impeller assembly housing.

In an Example 10, the blood pump of any of Examples 2-9, wherein the bearing assembly comprises: a first bearing that contacts the shaft and the impeller assembly housing; and a second bearing that contacts the first bearing and the impeller.

In an Example 11, a blood pump comprises: a magnetic field source; an impeller assembly including a longitudinal axis, an impeller, and a driven magnet, the driven magnet being longitudinally offset and distally disposed relative to the magnetic field source, the driven magnet being rotatable and longitudinally controlled by the magnetic field source; and a bearing assembly coupled to the impeller assembly, wherein no portion of the bearing assembly is located between the driven magnet and the magnetic field source.

In an Example 12, the blood pump of Example 11, further comprising an impeller assembly housing, the bearing assembly being in contact with the impeller assembly housing, and the impeller assembly housing rotatably carrying the impeller assembly via the bearing assembly.

In an Example 13, the blood pump of Example 12, wherein the impeller assembly housing includes a recess that receives the bearing assembly.

In an Example 14, the blood pump of any of Examples 12-13, wherein the bearing assembly comprises: a first bearing that contacts the shaft and the impeller assembly housing; and a second bearing that contacts the first bearing and the impeller.

In an Example 15, the blood pump of any of Examples 11-14, wherein the bearing assembly comprises a magnet bearing encapsulating the driven magnet.

In an Example 16, a blood pump comprises an impeller assembly housing; a magnetic field source coupled to the impeller assembly housing; an impeller assembly within the impeller assembly housing and including a longitudinal axis, an impeller, and a driven magnet, the driven magnet being longitudinally offset and distally disposed relative to the magnetic field source, the driven magnet being rotatable and longitudinally controlled by the magnetic field source, and the driven magnet comprising a distal side, the distal side facing the impeller; and a bearing assembly within and in contact with the impeller assembly housing and near the distal side of the driven magnet.

In an Example 17, the blood pump of Example 16, wherein the impeller assembly housing includes a recess that receives the bearing assembly.

In an Example 18, the blood pump of Example 16, wherein the distance between the magnetic field source and the driven magnet is less than 0.030 inches.

In an Example 19, the blood pump of Example 16, wherein the impeller assembly has a center of mass and the bearing assembly is aligned longitudinally with the center of mass of the impeller assembly.

In an Example 20, the blood pump of Example 16, wherein no portion of the bearing assembly is located between the driven magnet and the magnetic field source.

In an Example 21, the blood pump of Example 16, wherein the impeller assembly housing contains no bearing assembly located at a distal end of the impeller.

In an Example 22, the blood pump of Example 16, wherein the impeller assembly is rotatable about a longitudinal axis, and the bearing assembly is disposed radially outwardly relative to the longitudinal axis.

In an Example 23, the blood pump of Example 16, wherein the impeller assembly further includes a shaft, and the bearing assembly contacts the shaft and the impeller assembly housing.

In an Example 24, the blood pump of Example 23, wherein the bearing assembly comprises: a first bearing that contacts the shaft and the impeller assembly housing; and a second bearing that contacts the first bearing and the impeller.

In an Example 25, the blood pump of Example 23, wherein the shaft is coupled to and rotatable with the impeller.

In an Example 26, a blood pump comprises an impeller assembly housing; a magnetic field source coupled to the impeller assembly housing; an impeller assembly within the impeller assembly housing and including a longitudinal axis, an impeller, and a driven magnet, the driven magnet being longitudinally offset and distally disposed relative to the magnetic field source, the driven magnet being rotatable by the magnetic field source; and a bearing assembly within and in contact with the impeller assembly housing and coupled to the impeller assembly, wherein no portion of the bearing assembly is located between the driven magnet and the magnetic field source.

In an Example 27, the blood pump of Example 26, wherein the impeller assembly further includes a shaft.

In an Example 28, the blood pump of Example 27, wherein the bearing assembly contacts the shaft and the impeller assembly housing.

In an Example 29, the blood pump of Example 27, wherein the shaft is coupled to and rotatable with the impeller.

In an Example 30, the blood pump of Example 26, wherein the impeller assembly housing includes a recess that receives the bearing assembly.

In an Example 31, the blood pump of Example 26, wherein the bearing assembly comprises a magnet bearing encapsulating the driven magnet.

In an Example 32, the blood pump of Example 26, wherein the impeller assembly housing contains no bearing assembly located at a distal end of the impeller.

In an Example 33, a method of assembling a blood pump comprises coupling an impeller assembly to a bearing assembly such that the bearing assembly is near a distal side of a driven magnet and the distal side of the driven magnet faces an impeller of the impeller assembly; coupling the bearing assembly to an impeller assembly housing such that the bearing assembly is in contact with the impeller assembly housing and the driven magnet is longitudinally offset and distally disposed relative to a magnetic field source.

In an Example 34, the method of Example 33, wherein coupling the impeller assembly to the bearing assembly comprises contacting a shaft of the impeller assembly with the bearing assembly.

In an Example 35, the method of Example 33, wherein coupling the bearing assembly to the impeller assembly housing comprises positioning the bearing assembly in a recess of the impeller assembly housing.

While multiple embodiments are disclosed, still other embodiments will become apparent to those skilled in the art from the following detailed description, which shows and describes illustrative embodiments of the invention. Accordingly, the drawings and detailed description are to be regarded as illustrative in nature and not restrictive.

Figure 1A:
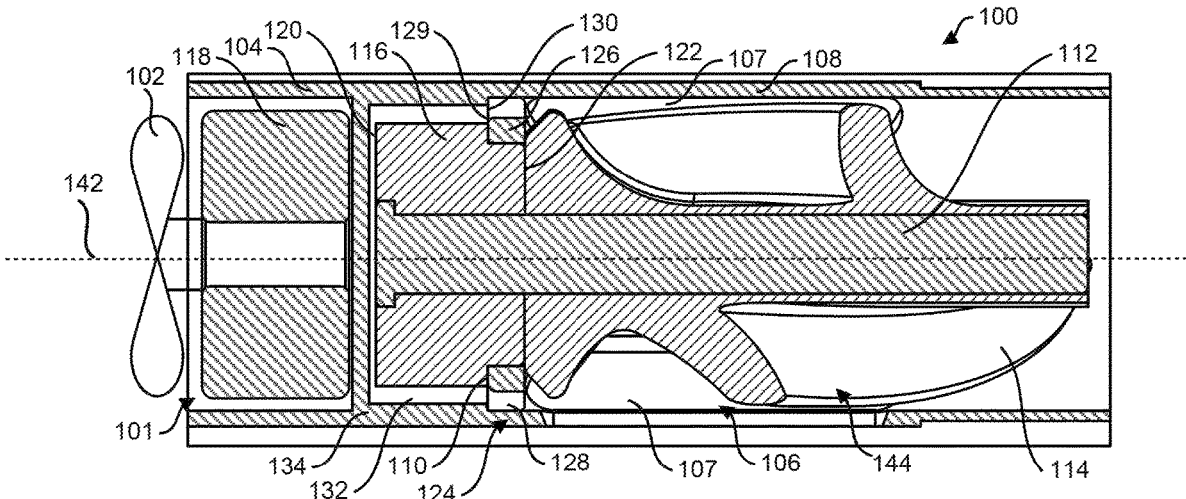
FIG. 1A depicts a cross-sectional side view of a portion of an illustrative percutaneous mechanical circulatory support device (also referred to herein, interchangeably, as a "blood pump"), in accordance with embodiments of the subject matter disclosed herein.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.)), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

DETAILED DESCRIPTION

Embodiments of the subject matter disclosed herein include blood pump and bearing designs that may facilitate reduction of the number of bearing surfaces and reduction in the number or size of magnets incorporated into percutaneous circulatory support devices. Reduction in the number of bearing surfaces within the blood pump may offer numerous advantages, including reducing the potential for hemolysis and other health complications. Embodiments of the subject matter disclosed herein include blood pump and bearing designs that improve magnetic torque transfer which can be used to increase blood flow rates, reduce risk of magnet corrosion, and improve durability of the blood pump. In addition, embodiments disclosed herein offer improved stability and efficiency of blood pump components for improved therapeutic performance.

Figure 1B:
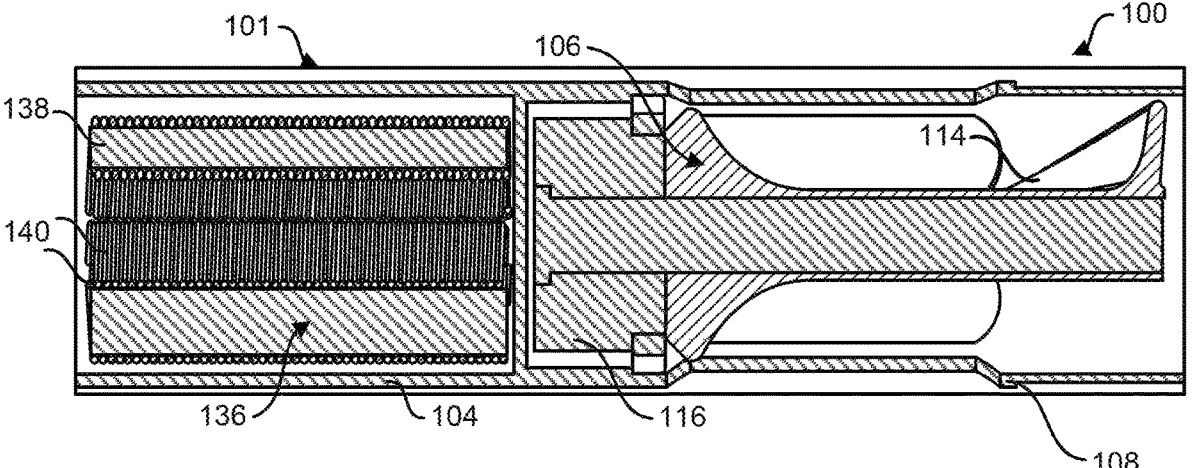
FIG. 1B depicts a cross-sectional view of an embodiment of an illustrative percutaneous mechanical circulatory support device, in accordance with embodiments of the subject matter disclosed herein.

FIG. 1A depicts a cross-sectional side view of a portion of an illustrative percutaneous mechanical circulatory support device 100 (also referred to herein, interchangeably, as a "blood pump"), in accordance with embodiments of the subject matter disclosed herein. The blood pump 100 includes a magnetic driving housing 104, which contains a magnetic field source 101. The magnetic field source 101 is configured to produce a varying magnetic field to drive rotation of an impeller 114 to provide a flow of blood through a blood pump 100. In the embodiment shown in FIG. 1A, the magnetic field source 101 includes a permanent driving magnet 118 rotating on a motor 102 and configured to cause rotation of a permanent driven magnet 116 coupled to the impeller 114 to provide a flow of blood through the blood pump 100. In alternative embodiments, the driving magnet 118 may be replaced by any type of magnetic rotor. For example, as shown in FIG. 1B and described below, the magnetic field source may include a set of electromagnetic coils configured to cause rotation of a permanent driven magnet coupled to an impeller to provide a flow of blood through the blood pump 100. In other alternative embodiments, magnetic field source may include a stator and motor for generating a magnetic field.

A controller (not shown) is operably coupled to the motor 102 and is configured to control the motor 102. The controller may be disposed within the magnetic driving housing 104 in embodiments, or in other embodiments, may be disposed outside the magnetic driving housing 104 (e.g., in a catheter handle, independent housing, etc.). In embodiments, the controller may include multiple components, one or more of which may be disposed within the magnetic driving housing 104. According to embodiments, the controller may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. Although the controller is referred to herein in the singular, the controller may be implemented in multiple instances, distributed across multiple computing devices, instantiated within multiple virtual machines, and/or the like.

As shown in FIG. 1A, an impeller assembly 106 is disposed within an impeller assembly housing 108, which includes an inlet aperture (not shown) and a number of outlet apertures 107 defined therein. A longitudinal axis 142 extends through impeller assembly 106. According to embodiments, the magnetic driving housing 104 and the impeller assembly housing 108 may be integrated with one another. In other embodiments, the magnetic driving housing 104 and the impeller assembly housing 108 may be separate components configured to be coupled together, either removably or permanently.

In FIG. 1A, the impeller assembly 106 includes the impeller 114 and the driven magnet 116 coupled to the impeller 114. The driven magnet 116 has a proximal side 120 and a distal side 122. The driven magnet 116 may be coupled distally to the impeller 114 as shown in FIG. 1A. The driven magnet 116 and the impeller 114 may be coupled in various ways, including through the use of adhesive, mechanically coupling, or interference fit. The driven magnet 116 may be any type of magnetic rotor capable of being driven by the driving magnet 118. As a magnetic field is applied to the driven magnet 116 by the driving magnet 118, the driven magnet 116 rotates, causing the impeller assembly 106 to rotate. Rotation of the impeller 114 causes blood flow through the blood pump 100.

As shown in FIG. 1A, the driven magnet 116 and the impeller 114 may be coupled via a drive shaft 112 coupled to the impeller 114 and configured to rotate with the impeller 114. The driven magnet 116 may be coupled to the drive shaft 112 and the impeller 114 in a variety of ways, including through the use of adhesive, mechanical coupling, or interference fit. The drive shaft 112 may be at least partially disposed within the impeller 114. The drive shaft 112 may also be at least partially surrounded by the driven magnet 116. The drive shaft 112 may be made of any number of different rigid materials such as, for example, steel, titanium alloys, cobalt chromium alloys, nitinol, high-strength ceramics, and/or the like.

FIG. 1B shows an alternative embodiment of a magnetic field source 101 that includes a stator electromagnetic driving coil assembly 136 electrically coupled to a power source (not shown). In such an embodiment, the driving coil assembly 136 may be axially aligned or circumferentially surrounding the driven magnet 116 and is configured to drive the driven magnet 116. The driving coil assembly 136 includes a ferromagnetic core 138 and a number of coil windings 140. The electromagnetic field could be generated from copper, graphene, or other high electrical conductivity materials in coiled configurations. The driving coil assembly 136 may include any number of coil windings 140 arranged in any number of configurations within the magnetic driving housing 104. As shown, the driving coil assembly 136 is disposed within a magnetic driving housing 104 and may be axially aligned or circumferentially surrounding the driven magnet 116. The magnetic driving housing 104 and the impeller assembly housing 108 are integrated in the illustrated embodiment and contains the magnetic field source 101 and the impeller assembly 106, including the driven magnet 116.

Figure 1C:
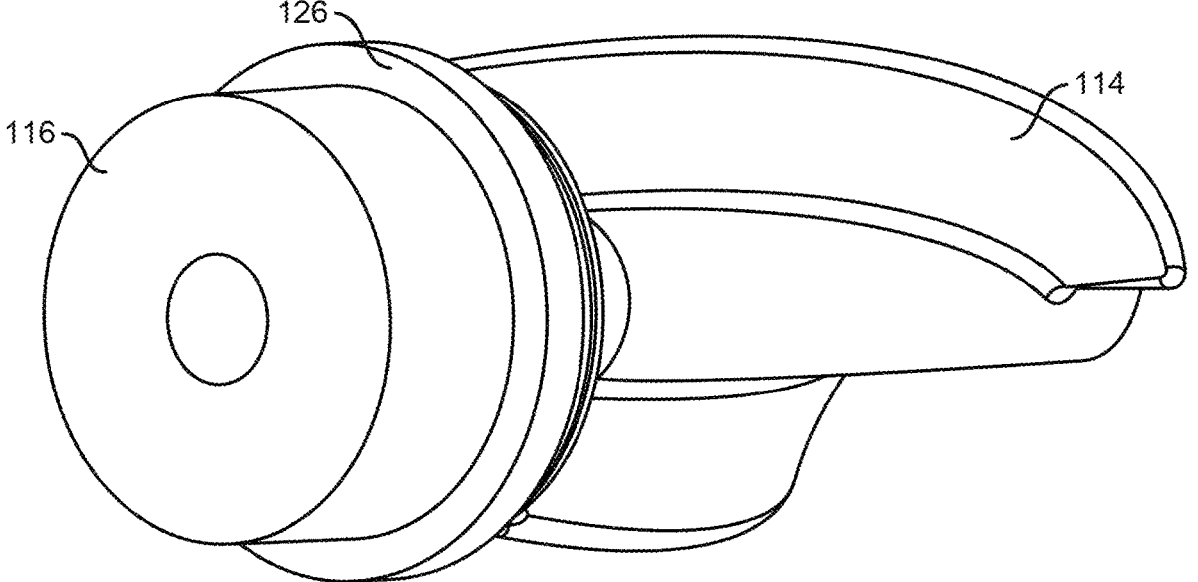
FIG. 1C depicts a perspective view of a portion of the illustrative percutaneous mechanical circulatory support device in FIG. 1A, in accordance with embodiments of the subject matter disclosed herein.

As shown in FIG. 1A, the impeller assembly 106, including the driven magnet 116, is retained within the impeller assembly housing 108 by a bearing assembly 124. According to embodiments, the bearing assembly 124 may be located near the distal side 122 of the driven magnet 116. FIG. 1C is a perspective view of the driven magnet 116, the magnet bearing 126, and the impeller 114, in accordance with embodiments of the subject matter disclosed herein.

Various embodiments of bearing assemblies for use in blood pumps are described herein. For example, as shown in FIG. 1A, the bearing assembly 124 may include a magnet bearing 126 and a housing bearing 128. According to embodiments, the bearing assembly 124 may include different types of bearings. The bearing assembly 124 may also include lubrication, while in other embodiments, the bearing assembly 124 may be free of lubrication. As shown, the bearing assembly 124 has a proximal side 130 contacting a distal shoulder 110 of the driven magnet 116. As shown, the housing bearing 128 includes a proximal inner lip 129 that contacts the magnet bearing 126. The proximal inner lip 129 carries a thrust load and inhibits the driven magnet 116 from bottoming out against a proximal end 134 of the impeller assembly housing 108.

As shown in FIG. 1A, the bearing assembly 124, including the magnet bearing 126 and the housing bearing 128, is positioned to be longitudinally near the center of mass of the impeller assembly 106. Mounting the magnet bearing 126 near the distal side 122 of the driven magnet 116 enables the bearing assembly 124 to be positioned close to the center of mass of the impeller assembly 106. The bearing assembly 124 is optimized when the magnet bearing 126 and housing bearing 128 are aligned with the center of mass of the impeller assembly 106. Positioning the bearing assembly 124 longitudinally near the center of mass of the impeller assembly 106 increases radial control of the impeller assembly 106 and protects against eccentric motion of the impeller 114 as compared with a bearing assembly that relies on bearing assemblies both proximal and distal to the impeller assembly 106. The location of the bearing assembly 124 may deviate approximately 0.050 inches from the center of mass of the impeller assembly 106 based on practical considerations for part assembly, but is optimized when located longitudinally as close as possible to the center of mass of the impeller assembly 106. The bearing assembly 124 is also configured to use forces parallel to the longitudinal axis of the impeller assembly 106 to counter the magnetic coupling axial force and prevent the driven magnet 116 from bottoming out against the proximal end 134 of the impeller assembly housing 108, thus providing axial control of the impeller assembly 106.

The center of mass of the impeller assembly 106 is contingent on both the design and material selection of the driven magnet 116, impeller 114, drive shaft 112, and any other materials used to assemble the components together. Suitable magnetic materials that may be used for the driven magnet 116, including neodymium iron boron and samarium cobalt, have densities five to six times greater than polymers, such as polyether ether ketone (PEEK), that may be used for the impeller 114. The driven magnet 116 thus likely constitutes greater than fifty percent of the total mass of the impeller assembly 106. The driven magnet 116 may have a reduced diameter portion such as a distal shoulder 110 to facilitate securement of the magnet bearing 126 to the driven magnet 116.

Figure 1D:
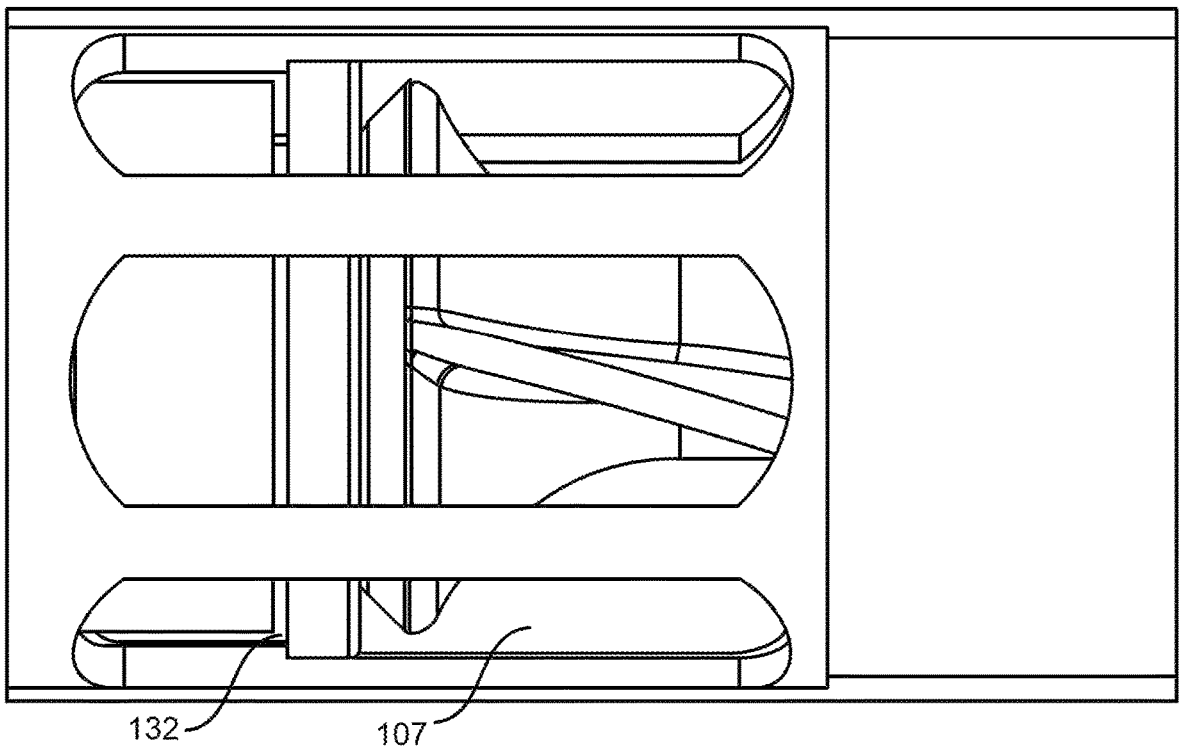
FIG. 1D depicts a side view of a portion of an embodiment of an illustrative percutaneous mechanical circulatory support device, in accordance with embodiments of the subject matter disclosed herein.

As shown in FIG. 1A, a cavity 132 is formed by the proximal side 130 of the bearing assembly 124, the impeller assembly housing 108, and the driven magnet 116. In embodiments, the size of the driven magnet 116 may be decreased to increase the spacing between the driven magnet 116 and the impeller assembly housing 108. In turn, the size of the cavity 132 may increase. Increasing the size of the cavity 132 reduces the shear stresses acting on the blood within the cavity 132. Lower shear stresses are associated with lower hemolysis and lower platelet activation which may result in lower rates of thrombus formation. In some embodiments, a liquid may be disposed within the cavity 132. The liquid may be any type of hydrophobic lubricant suitable for use in a blood pump. For example, in embodiments, but without intending to limit the disclosure, the liquid may be a biocompatible oil or modified silicone lubricant such as, for example, a modified polydimethylsiloxane (PDMS). In other embodiments, the liquid may be an oil-based lubricant, a synthetic oil, a carbon-based lubricant, and/or the like. The advantages of using a liquid in the cavity 132 include reducing the possibility of air embolization, limiting the exposure of blood to the driven magnet 116 in order to reduce hemolysis associated with the driven magnet 116, reducing the risk of thrombus formation and corrosion on the driven magnet through lower blood contact, and reducing hemolysis associated with the bearing assembly 124 through lubrication of the bearings 126, 128. In other embodiments, the cavity 132 can be left empty. In other embodiments, and as shown in FIG. 1D, the cavity 132 may be exposed to blood flow to facilitate constant blood circulation around the driven magnet 116, which may be beneficial in preventing thrombosis.

The blood pumps shown in FIGS. 1A and 1B may be assembled as follows. The bearing assembly 124 may be assembled by loading the magnet bearing 126 and the housing bearing 128 separately. The housing bearing 128 may be secured to the impeller assembly housing 108 via press fit, adhesive, mechanical coupling, sintering, welding or any method known by a person of ordinary skill in the art. Outside of the impeller assembly housing 108, the impeller assembly 106, including the driven magnet 116, may be coupled to the magnet bearing 126, with the magnet bearing 126 being secured to the driven magnet 116 via press fit, adhesive, mechanical coupling, sintering, welding or any method known by a person of ordinary skill in the art. The impeller assembly 106, including the driven magnet 116, and the coupled magnet bearing 126 may be collectively referred to as the impeller-magnet-bearing assembly 144. The impeller-magnet-bearing assembly 144 may then be positioned within the impeller assembly housing 108 such that the magnet bearing 126 mates with the housing bearing 128. In one embodiment, an outer diameter of the driven magnet 116 may be uniform and smaller in diameter than the inner diameter of the combination of the impeller assembly housing 108 and the housing bearing 128 so that the impeller-magnet-bearing assembly 144 fits within the combination of the housing bearing 128 and the impeller assembly housing 108. In other embodiments, and as shown in FIG. 1A and FIG. 1B, the outer diameter of the driven magnet 116 may be approximately the same as the outer diameter of the combination of the driven magnet 116 and the magnet bearing 126, except at the location where the magnet bearing 126 is secured to the driven magnet 116. For example, in such embodiments, the driven magnet 116 may include a reduced diameter portion, such as a distal shoulder 110, to accommodate the magnet bearing 126. The distal shoulder 110 may facilitate the securement of the bearing assembly 124 such that the bearing assembly 124 provides improved radial control to the impeller assembly 106.

The illustrative circulatory support device 100 shown in FIGS. 1A-1D is not intended to suggest any limitation as to the scope of use or functionality of embodiments of the present disclosure. The illustrative circulatory support device 100 also should not be interpreted as having any dependency or requirement related to any single component or combination of components illustrated therein. Additionally, various components depicted in FIGS. 1A-1D may be, in embodiments, integrated with various ones of the other components depicted therein (and/or components not illustrated), all of which are considered to be within the ambit of the present disclosure.

Figure 2A:
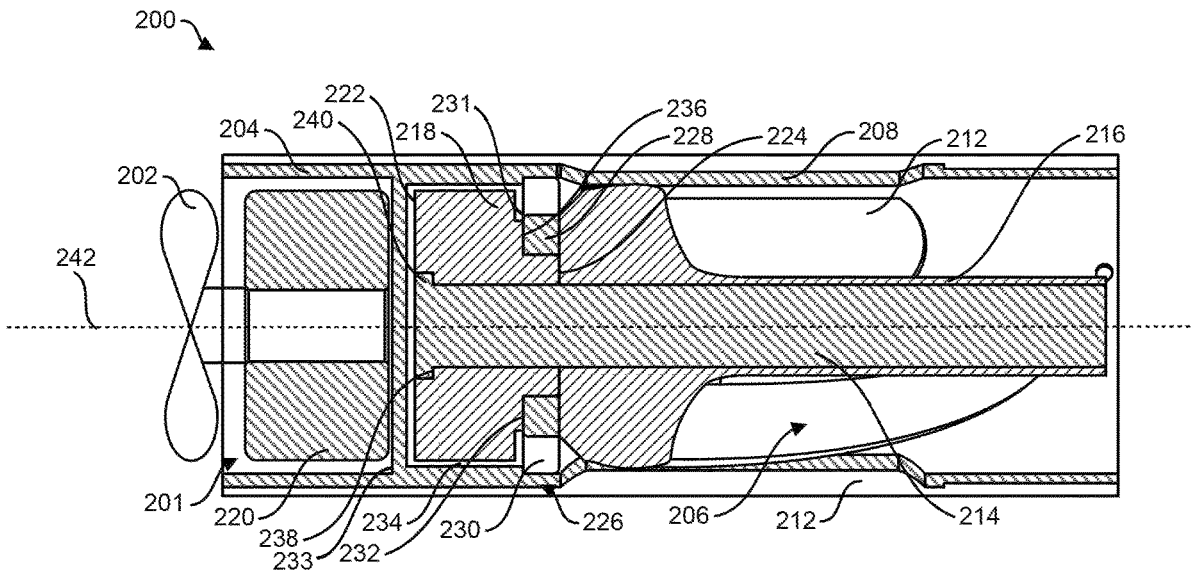
FIG. 2A depicts a cross-sectional side view of a circulatory support device, in accordance with embodiments of the subject matter disclosed herein.
Figure 2B:
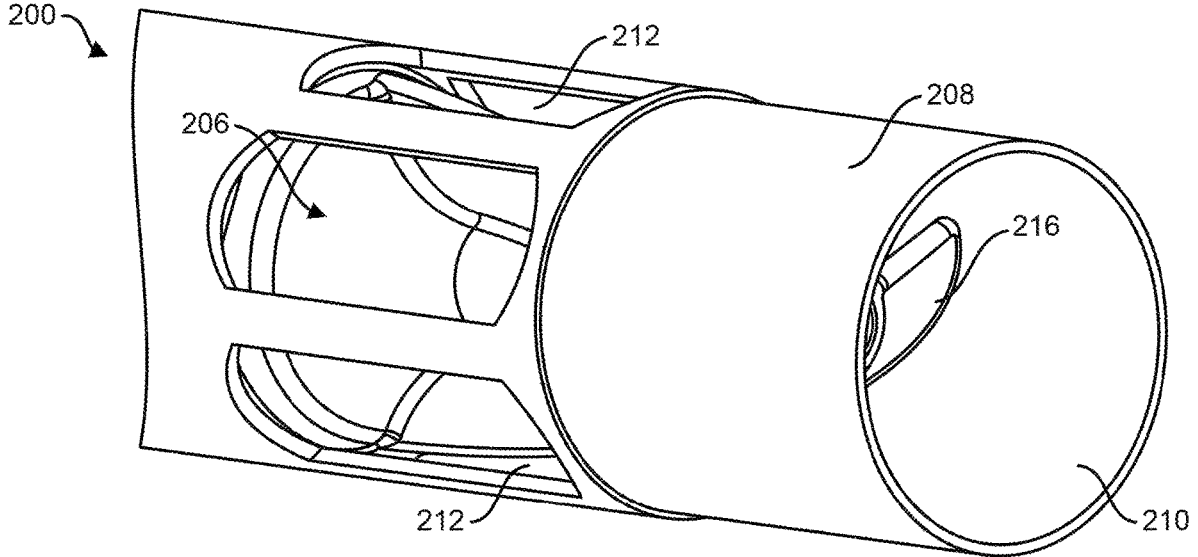
FIG. 2B depicts a perspective view of a portion of an illustrative percutaneous mechanical circulatory support device depicted in FIG. 2A, in accordance with embodiments of the subject matter disclosed herein.

FIG. 2A depicts a cross-sectional side view of an illustrative percutaneous mechanical circulatory support device 200 (also referred to herein, interchangeably, as a "blood pump"), in accordance with embodiments of the subject matter disclosed herein; and FIG. 2B depicts a perspective view of the blood pump 200 depicted in FIG. 2A, in accordance with embodiments of the subject matter disclosed herein. According to embodiments, the blood pump 200, and/or any number of various components thereof, may be the same as, or similar to, corresponding components of the circulatory support device 100 depicted in FIGS. 1A and 1B.

As shown in FIG. 2A, the blood pump 200 includes a magnetic driving housing 204, which contains a magnetic field source 201 configured to produce a varying magnetic field to drive rotation of an impeller 216 to provide a flow of blood through the blood pump 200. In the embodiment shown in FIG. 2A, the magnetic field source 201 includes a permanent driving magnet 220, rotating on a motor 202 and is configured to cause rotation of a permanent driven magnet 218 coupled to the impeller 216 to provide a flow of blood through the blood pump 200. As shown, the driven magnet 218 includes a proximal side 222 and a distal side 224. In alternative embodiments, as described above but not shown here, the magnetic field source 201 may include a set of electromagnetic coils or a stator and motor for generating a magnetic field to cause rotation a permanent driven magnet coupled to an impeller to provide a flow of blood through blood pump.

A controller (not shown) is operably coupled to the motor 202 and is configured to control the motor 202. The controller may be disposed within the magnetic driving housing 204 in embodiments, or in other embodiments, may be disposed outside the magnetic driving housing 204 (e.g., in a catheter handle, independent housing, etc.). In embodiments, the controller may include multiple components, one or more of which may be disposed within the magnetic driving housing 204. According to embodiments, the controller coupled to the motor 202 may be similar to the controller coupled to the motor 102 described under FIG. 1A.

As shown in FIG. 2A, an impeller assembly 206 is disposed within an impeller assembly housing 208, which includes an inlet aperture (not shown) and a number of outlet apertures 212 defined therein. A longitudinal axis 242 extends through impeller assembly 206. According to embodiments, the magnetic driving housing 204 and the impeller assembly housing 208 may be integrated with one another. In other embodiments, the magnetic driving housing 204 and the impeller assembly housing 208 may be separate components configured to be coupled together, either removably or permanently. The impeller assembly 206 includes an impeller 216 and a driven magnet 218 coupled to the impeller 216. The driven magnet 218 and the impeller 216 may be coupled in multiple ways, including through the use of adhesive, mechanical coupling, or interference fit. The driven magnet 218 may be any type of magnetic rotor capable of being driven by a driving magnet 220. As a magnetic field is applied to the driven magnet 218 by the driving magnet 220, the driven magnet 218 rotates, causing the impeller 216 to rotate. Rotation of the impeller 216 causes blood flow through the blood pump 200.

FIG. 2B depicts a perspective view of the blood pump 200 depicted in FIG. 2A, in accordance with embodiments of the subject matter disclosed herein. As shown, the impeller assembly 206, including the impeller 216, is disposed within the impeller assembly housing 208, which includes an inlet aperture 210 and a number of outlet apertures 212.

As shown in FIG. 2A, the driven magnet 218 and the impeller 216 may be coupled via a drive shaft 214 coupled to the impeller 216 and configured to rotate with the impeller 216. The driven magnet 218 may be coupled to the drive shaft 214 and the impeller 216 in a variety of ways, including through the use of adhesive, mechanical coupling, or interference fit. The drive shaft 214 may be at least partially disposed within the impeller 216. The drive shaft 214 may also be at least partially surrounded by the driven magnet 218. The drive shaft 214 may be made of any number of different rigid materials such as, for example, steel, titanium alloys, cobalt chromium alloys, nitinol, high-strength ceramics, and/or the like.

As shown in FIG. 2A, the impeller assembly 206, including the driven magnet 218, is retained within the impeller assembly housing 208 by a bearing assembly 226. According to embodiments, the bearing assembly 226 may be located near the distal side 224 of the driven magnet 218. According to embodiments, the bearing assembly 226 may include different types of bearings. The bearing assembly 226 may also include lubrication, while in other embodiments, the bearing assembly 226 may be free of lubrication. As shown in FIG. 2A, the bearing assembly 226 includes a magnet bearing 228 and a housing bearing 230. The driven magnet 218 may have a reduced diameter portion such as a distal shoulder 236 to facilitate securement of the magnet bearing 228 to the driven magnet 218. As shown, the bearing assembly 226 has a proximal side 232 contacting the distal surface of the distal shoulder 236 of the driven magnet 218. As shown, the housing bearing 230 includes a proximal inner lip 231 that contacts the magnet bearing 228. The proximal inner lip 231 carries a thrust load and inhibits the driven magnet 218 from bottoming out against a proximal end 233 of the impeller assembly housing 208.

As described above with respect to FIG. 2A, the bearing assembly 226, including the magnet bearing 228 and the housing bearing 230, is positioned to be longitudinally near the center of mass of the impeller assembly 206. The bearing assembly 226 is optimized when the magnet bearing 228 and housing bearing 230 are aligned with the center of mass of the impeller assembly 206. The location of the bearing assembly 226 may deviate approximately 0.050 inches from the center of mass of the impeller assembly 206 based on practical considerations for part assembly, but is optimized when located longitudinally as close as possible to the center of mass of the impeller assembly 206.

As shown in FIG. 2A, a cavity 234 is formed by the proximal side 232 of the bearing assembly 226, the impeller assembly housing 208, and the driven magnet 218. By increasing the size of the driven magnet 218 as compared to the driven magnet 116 shown in FIG. 1A, the size of the cavity 234 is decreased as compared to the cavity 132 shown in FIG. 1A. In some embodiments, a liquid may be disposed within the cavity 234, as described above. In other embodiments, the cavity 234 can be left empty.

According to one embodiment shown in FIG. 2A, the magnet bearing 228 may be loaded onto the housing bearing 230 outside the impeller assembly housing 208, such that the distal faces of the magnet bearing 228 and housing bearing 230 are flush with each other. The distal side 224 of the driven magnet 218 may then be coupled to the proximal side of the magnet bearing 228. The magnet bearing 228 and the driven magnet 218 may be coupled via press fit, adhesive, mechanical coupling, sintering, welding or any method known by a person of ordinary skill in the art. As shown, the driven magnet 218 may include a proximal shoulder 238 and the drive shaft 214 may include a head 240. The drive shaft 214 may be placed through the proximal inner diameter of the driven magnet 218 until the drive shaft head 240 bottoms out against the proximal shoulder 238 of the driven magnet 218 and coupled in place as described above. The impeller 216 may then be loaded onto the drive shaft 214 and coupled in place via press fit, adhesive, mechanical coupling, sintering, welding or any method known by a person of ordinary skill in the art. The order of coupling the drive shaft 214 and the impeller 216 may be reversed from described above. In other embodiments, the drive shaft 214 may be eliminated and the impeller 216 may be coupled to the driven magnet 218 in place via press fit, adhesive, mechanical coupling, sintering, welding or any method known by a person of ordinary skill in the art. The impeller assembly 206 and the bearing assembly 226 can then be loaded into the impeller assembly housing 208 and coupled in place via press fit, adhesive, mechanical coupling, sintering, welding or any method known by a person of ordinary skill in the art.

As shown, the outer diameter of the driven magnet 218 may be larger than the inner diameter of the housing bearing 230, except at the location where the magnet bearing 228 is secured to the driven magnet 218. For example, in such embodiments, the driven magnet 218 may include a reduced diameter portion, such as the distal shoulder 236, to accommodate the magnet bearing 228 and housing bearing 230 such that the outer diameter of the combination of the driven magnet 218, the magnet bearing 228, and the housing bearing 230 are approximately the same as the outer diameter of the remainder of the driven magnet 218. In other words, the outer diameter of the driven magnet 218 may closely approximate the inner diameter of the impeller assembly housing 208, except at the distal shoulder 236 of the driven magnet 218. By increasing the size of the distal shoulder 236 and loading the magnet bearing 228 and the housing bearing 230 onto the driven magnet 218, a larger driven magnet may be used compared to the embodiment shown in FIG. 1A. In addition, the size and/or thickness of the bearing assembly 226 may be adjusted. In some embodiments, the bearing assembly 226 may be thicker to maintain its mechanical integrity and durability.

The illustrative circulatory support device 200 shown in FIGS. 2A-2B is not intended to suggest any limitation as to the scope of use or functionality of embodiments of the present disclosure. The illustrative circulatory support device 200 also should not be interpreted as having any dependency or requirement related to any single component or combination of components illustrated therein. Additionally, various components depicted in FIGS. 2A-2B may be, in embodiments, integrated with various ones of the other components depicted therein (and/or components not illustrated), all of which are considered to be within the ambit of the present disclosure.

Previous magnetically driven blood pumps have been known to incorporate at least two bearing assemblies, positioning one bearing assembly near the proximal end of the impeller assembly and another bearing assembly near the distal end of the impeller assembly to control the longitudinal and radial motion of the impeller assembly. Such designs having bearings mounted on the longitudinal ends of the impeller are based on having bearings that incorporate a feature that imparts force orthogonal to the longitudinal axis to prevent the impeller from moving in either direction longitudinally. A radiused feature or journal bearing-like feature is incorporated on the distal and proximal bearings to control radial motion. Such designs usually achieve rotational control of the impeller through a total of four to six blood contacting components. In such designs, the bearing assembly near the proximal end of the impeller assembly may be positioned in between the magnetic field source and the driven magnet.

One advantage of positioning the bearing assemblies 124, 226 longitudinally near the center of mass of the impeller assemblies 106, 206, as shown in the embodiments of FIGS. 1A-2B, is that no bearing is necessarily required between the driven magnets 116, 218 and the magnetic field sources 101, 201. Consequently, the driven magnets 116, 218 and the magnetic field sources, 101, 201 may be positioned closer together than in designs where a bearing assembly is located at the proximal end of the impeller assemblies. For example, in the embodiments shown in FIGS. 1A-2B, the distance between the driving magnets 118, 220 and the magnetic field sources 101, 201 could be as little as 0.012 inches, and preferably less than 0.030 inches. By reducing the distance between the driven magnets 118, 220 and magnetic field sources 101, 201, less magnetic flux is lost to space, which increases the magnetic torque transfer. The improved capture of magnetic flux from the magnetic field sources 101, 201 by reducing the spatial distance from the magnetic field sources 101, 201 to the driven magnets 116, 218 enables more torque for higher flow rate designs, use of more corrosion resistant magnets, and smaller form factors. Reduction of the distance between the driven magnets 116, 218 and the magnetic field sources 101, 201 may increase magnetic torque transferred to the driven magnets 116, 218 by over 100%. The reduced spacing of the magnetic field sources and driven magnets also permits use of non-mechanically contacting magnetic fields to control longitudinal forces, impeller rotation, and stability. In addition, such arrangements may improve magnet durability. Also, reduction of the distance between the magnetic field sources 101, 201 to the driven magnets 116, 218 may allow for the use of mechanical encasings on the driven magnets 116, 218, as shown below in connection with FIGS. 3A-3B, or the use of a more corrosion resistant magnet material such as samarium cobalt, or the use of more durable magnets with lower magnetic strength. Such arrangements may also provide the opportunity to improve power efficiency of blood pumps powered by batteries.

In addition, reduction of the distance between the magnetic field sources 101, 201 and driven magnets 116, 218 may permit the use of smaller driving magnets, improved efficiency from electromagnetic coils, and/or smaller driven magnets to produce the same blood flow rates as designs incorporating larger driving magnets and driven magnets separated by greater distances. The flow rate of the blood pumps is dependent upon, among other factors, torque transfer, the overall pump design, including impeller size, operating speed, and the design of the impeller and the flow lumen which determine the flow profile. For a given pump design and target flow rate, there is an amount of torque required to drive the impeller assemblies. The magnetic coupling must be able to transfer this amount of torque. The amount of torque that can be transferred is a function of magnet size and spacing. In general, greater torque can be transmitted with larger magnets and/or magnets which are spaced closer together. In some embodiments, the size of the driving magnets and/or driven magnets may be adjusted to match the torque requirements of the desired flow rate from the blood pumps. Other considerations may impact magnet size, including blood pump form factor, magnet material, and contribution of the magnet(s) to hemolysis. A reduction in size of the driven magnets may also reduce the amount of hemolysis caused by the use of the blood pumps, for example, by allowing for a greater amount of space between the impeller assembly housings and the driven magnets, and thus reducing the shear stresses acting on the blood within such areas as cavities 132, 234.

Another advantage of the embodiments shown in FIGS. 1A-2B is that the impeller assemblies 106, 206 may be controlled both longitudinally and radially with only one bearing assembly. As noted above, previous blood pumps have been known to incorporate at least two bearing assemblies, often positioning one bearing assembly near the proximal end of the impeller assembly and another bearing assembly near the distal end of the impeller assembly, to control the longitudinal and radial motion of the impeller assembly. In contrast, by requiring only one bearing assembly, embodiments disclosed herein reduce the number of blood-contacting bearing assemblies, and preferably reduce the number of bearings down to two. Reducing the number of surfaces exposed to blood reduces risks of hemolysis and thrombosis caused by blood interacting with bearing surfaces. Such arrangements also simplify assembly of the blood pump and may also reduce the rigid length of the blood pump, which may improve the delivery of a percutaneous-based device. Simplification of the number of components that interact in a tightly controlled manner is also beneficial to manufacturability of the blood pump and its components.

Another related advantage of the embodiments disclosed herein is that the bearing assemblies 124, 226 are positioned or aligned longitudinally near the center of mass of the impeller assemblies 106, 206 and such positioning improves the overall radial stability of the impeller assemblies 106, 206 by controlling the motion of the impeller assemblies 106, 206 at a location close to the centroid of the impeller assemblies 106, 206. Such positioning of the bearing assemblies 124, 226 also may protect against component imbalance that causes eccentric impeller motion which may result in increased shear rates on the blood flowing through the blood pumps 100, 200.

Figure 3A:
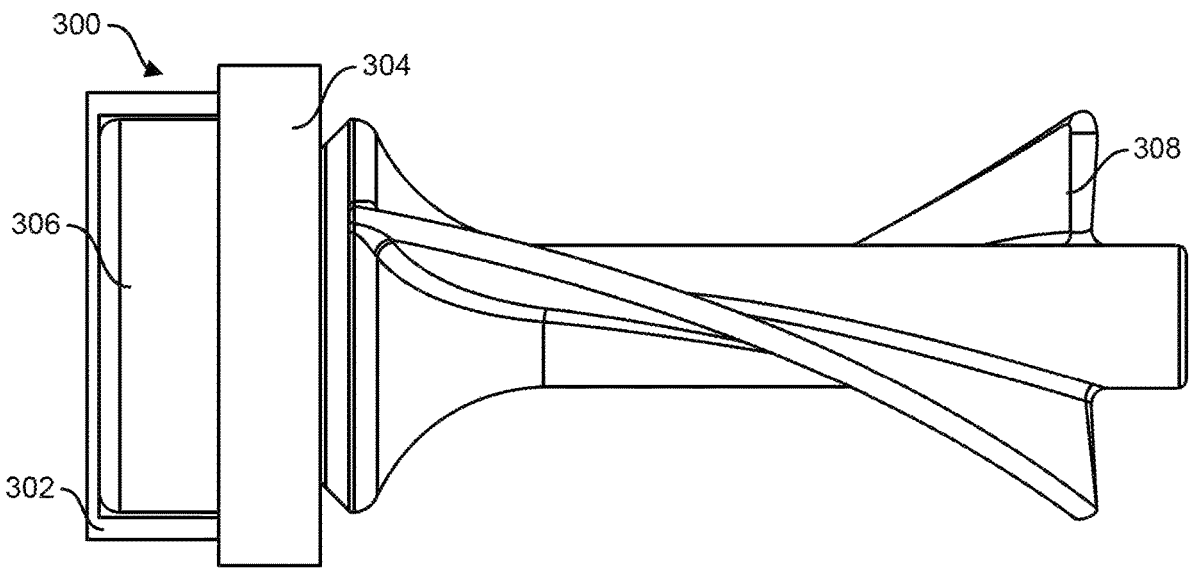
FIG. 3A depicts a perspective view of an embodiment of a bearing assembly, in accordance with embodiments of the subject matter disclosed herein.
Figure 3B:
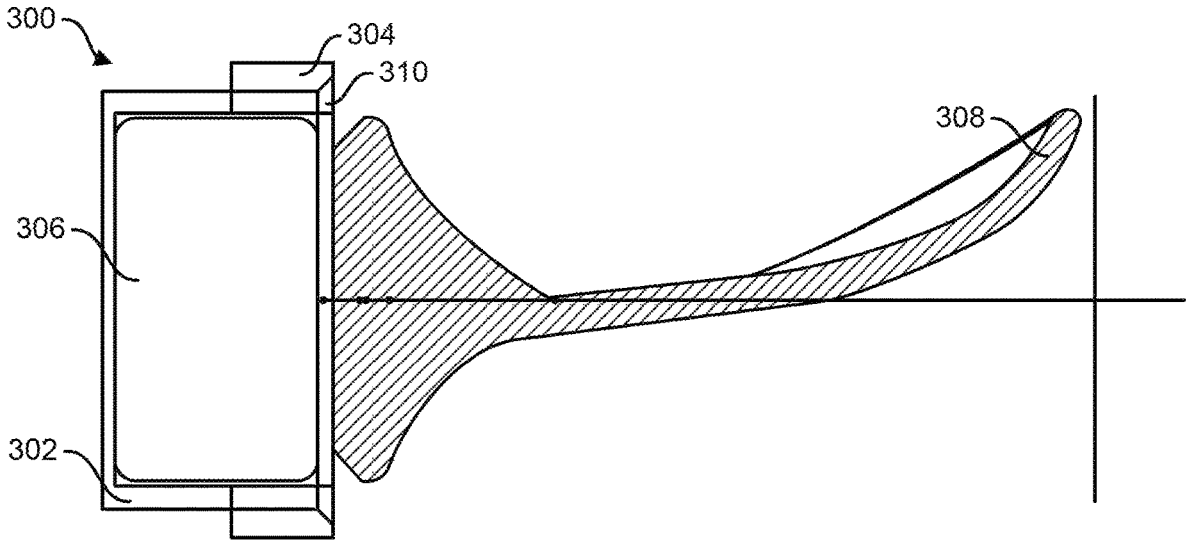
FIG. 3B depicts a cross-sectional side view of the bearing assembly depicted in FIG. 3A, in accordance with embodiments of the subject matter disclosed herein.

FIG. 3A depicts a perspective view of an embodiment of a bearing assembly 300, in accordance with embodiments of the subject matter disclosed herein; and FIG. 3B depicts a cross-sectional side view of the bearing assembly 300 depicted in FIG. 3A, in accordance with embodiments of the subject matter disclosed herein. According to embodiments, the bearing assembly 300, and/or any number of various components thereof, may be the same as, or similar to, corresponding components of the circulatory support device 100 depicted in FIGS. 1A-1D, and/or the circulatory support device 200 depicted in FIGS. 2A-2B.

As shown in FIGS. 3A and 3B, the bearing assembly 300 includes a magnet bearing 302 and a housing bearing 304. The magnet bearing 302 fully encapsulates a driven magnet 306 and may act as a hermetic seal for the driven magnet 306. The housing bearing 304 is located near an impeller 308 and mounted on an impeller assembly housing (not shown). The driven magnet 306 may be made of material such as Ne—Fe—B (neodymium), which is a material susceptible to corrosion upon contacting blood. The bearing assembly 300, including the magnet bearing 302 and housing bearing 304, may be made of materials resistant to corrosion, such as silicone nitride, sapphire, Vespel, torlon, PTFE, or any other material resistant to corrosion known by a person of ordinary skill in the art. Thus, in some embodiments, the fully encapsulated driven magnet 306 is less susceptible to corrosion and has increased durability. In other embodiments, the driven magnet 306 itself could be made of samarium cobalt to improve corrosion resistance and durability.

As shown in FIG. 3B, the magnet bearing 302 may fit into the housing bearing 304 through a wedge shape 310. In some embodiments, the shape could be of a "U" or "V." In other embodiments, the fit could be of an alternative design that combines longitudinal and radial control through alternative angled contact designs. In still other embodiments, the magnet bearing 302 and housing bearing 304 may be designed to prevent the build-up of heat, friction, or other issues detrimental to the operation or structural integrity of the bearing assembly 300.

The illustrative bearing assembly 300 shown in FIGS. 3A and 3B is not intended to suggest any limitation as to the scope of use or functionality of embodiments of the present disclosure. The illustrative bearing assembly 300 also should not be interpreted as having any dependency or requirement related to any single component or combination of components illustrated therein. Additionally, various components depicted in FIGS. 3A and 3B may be, in embodiments, integrated with various ones of the other components depicted therein (and/or components not illustrated), all of which are considered to be within the ambit of the present disclosure.

Figure 4:
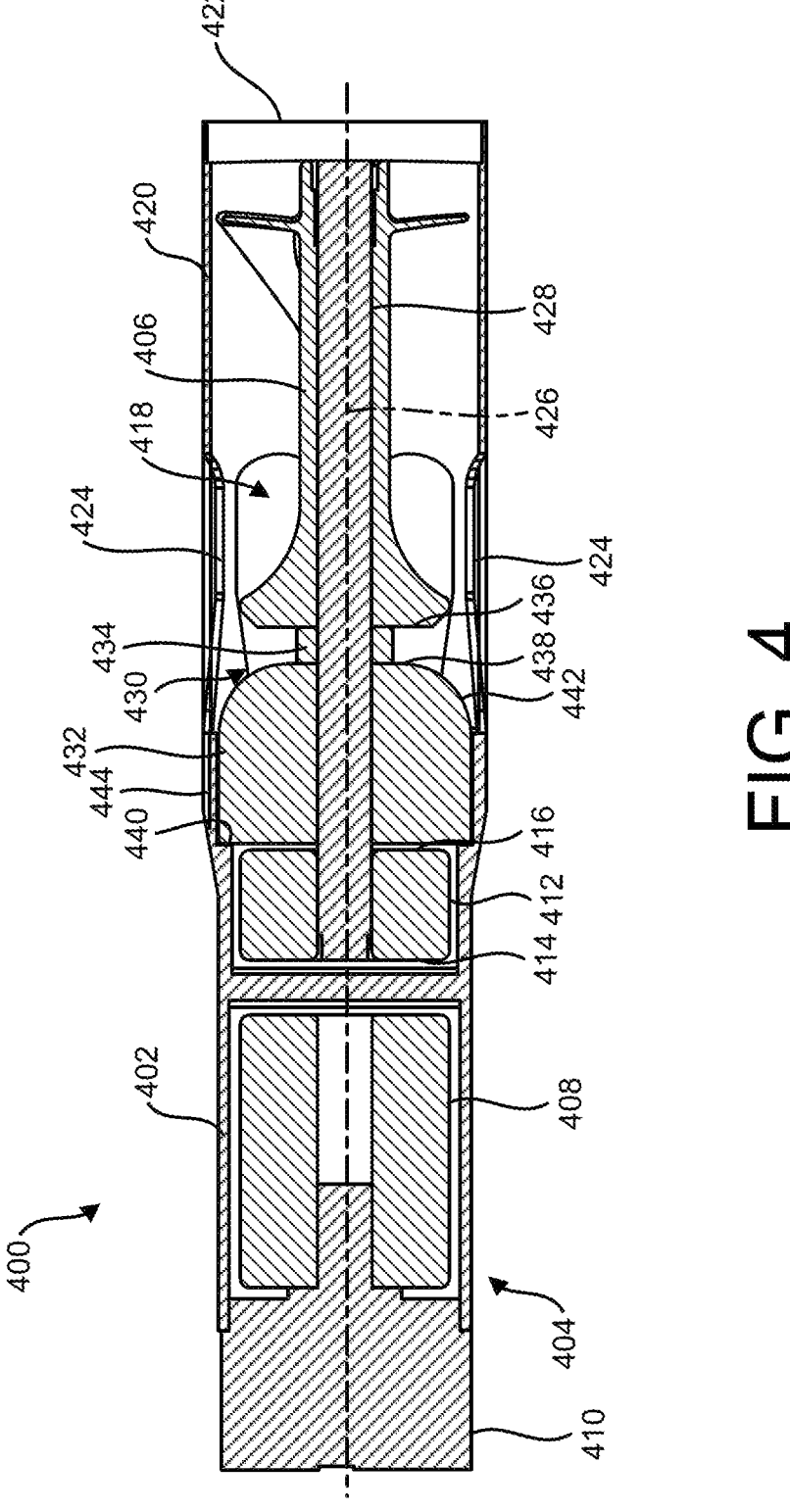
FIG. 4 depicts a cross-sectional view of another embodiment of an illustrative percutaneous mechanical circulatory support device, in accordance with embodiments of the subject matter disclosed herein.

FIG. 4 depicts a cross-sectional side view of an illustrative percutaneous mechanical circulatory support device 400 (also referred to herein, interchangeably, as a "blood pump"), in accordance with embodiments of the subject matter disclosed herein. According to embodiments, the blood pump 400, and/or any number of various components thereof, may be the same as, or similar to, corresponding components of the circulatory support device 100 depicted in FIGS. 1A and 1B or the same as, or similar to, corresponding components of the circulatory support device 200 depicted in FIGS. 2A and 2B.

As shown in FIG. 4, the blood pump 400 includes a magnetic driving housing 402, which contains a magnetic field source 404 configured to produce a varying magnetic field to drive rotation of an impeller 406 to provide a flow of blood through the blood pump 400. In the embodiment shown in FIG. 4, the magnetic field source 404 includes a permanent driving magnet 408, rotated by a motor 410 and configured to cause rotation of a permanent driven magnet 412 coupled to the impeller 406 to provide a flow of blood through the blood pump 400. As shown, the driven magnet 412 includes a proximal side 414 and a distal side 416. In alternative embodiments, as described above but not shown here, the magnetic field source 404 may include a set of electromagnetic coils or a stator and motor for generating a magnetic field to cause rotation a permanent driven magnet coupled to an impeller to provide a flow of blood through blood pump.

A controller (not shown) is operably coupled to the motor 410 and is configured to control the motor 410. The controller may be disposed within the motor 410 in embodiments, or in other embodiments, may be disposed outside the motor 410 (e.g., in a catheter handle, independent housing, etc.). In some embodiments, the controller may include multiple components, one or more of which may be disposed within the motor 410. According to some embodiments, the controller coupled to the motor 410 may be similar to the controller coupled to the motor 102 described in connection with FIG. 1A.

As shown in FIG. 4, an impeller assembly 418 is disposed within an impeller assembly housing 420, which includes an inlet aperture 422 and a plurality of outlet apertures 424 defined therein. A longitudinal axis 426 extends through the impeller assembly 418. According to some embodiments and as illustrated, the magnetic driving housing 402 and the impeller assembly housing 420 may be integrated with one another. In other embodiments, the magnetic driving housing 402 and the impeller assembly housing 420 may be separate components configured to be coupled together, either removably or permanently. The impeller assembly 418 includes the impeller 406 and the driven magnet 412. The driven magnet 412 and the impeller 406 may be coupled in a variety of ways, including through the use of adhesive, mechanical coupling, or interference fit. The driven magnet 412 may be any type of magnetic rotor capable of being driven by the magnetic field source 404. As a magnetic field is applied to the driven magnet 412 by the magnetic field source 404, the driven magnet 412 rotates, causing the impeller 406 to rotate. Rotation of the impeller 406 causes blood flow through the blood pump 400.

As shown in FIG. 4, the driven magnet 412 and the impeller 406 may be coupled via a drive shaft 428 coupled to the impeller 406 and configured to rotate with the impeller 406. The driven magnet 412 may be coupled to the drive shaft 428 and the impeller 406 in a variety of ways, including through the use of adhesive, mechanical coupling, or interference fit. The drive shaft 428 may be at least partially disposed within the impeller 406. The drive shaft 428 may also be at least partially surrounded by the driven magnet 412. The drive shaft 428 may be made of any number of different rigid materials such as, for example, steel, titanium alloys, cobalt chromium alloys, nitinol, high-strength ceramics, and/or the like.

As shown in FIG. 4, the impeller assembly 418 is coupled to and retained within the impeller assembly housing 420 by a bearing assembly 430. According to some embodiments, the bearing assembly 430 may be located near the distal side 416 of the driven magnet 412. According to some embodiments, the bearing assembly 430 may include different types of bearings. The bearing assembly 430 may also include lubrication, while in other embodiments, the bearing assembly 430 may be free of lubrication. As shown in FIG. 4, the bearing assembly 430 includes a first bearing 432, which may also be referred to as a housing bearing, and a second bearing 434, which may also be referred to as a thrust bearing. The thrust bearing 434 rotates with the shaft 428 and the other components of the impeller assembly 418. The thrust bearing 434 contacts a proximal side 436 of the impeller 406 and a distal side 438 of the housing bearing 432. Bearing assembly 430, including the first bearing 432 and the second bearing 434, may be made of one or more materials resistant to corrosion, such as silicon nitride, ceramics, sapphire, Vespel, torlon, PTFE, or any other material resistant to corrosion known by a person of ordinary skill in the art.

With continued reference to FIG. 4, the housing bearing 432 contacts the impeller assembly housing 420. More specifically, the impeller assembly housing 420 includes a recess or pocket 440 that receives the housing bearing 432. The housing bearing 432 rotatably carries the shaft 428, and the housing bearing 432 includes a rounded outer corner 442 that reduces or minimizes hemolysis of blood flowing through the device 400. In some embodiments, by having the driven magnet 412 behind the housing bearing 432, the housing bearing 432 reduces or minimizes an amount of blood that contacts the driven magnet 412, which may facilitate reduced hemolysis. In some embodiments, the housing bearing 432 may be positioned to be longitudinally near the center of mass of the impeller assembly 418. The device 400 may be optimized when the housing bearing 432 is are aligned with the center of mass of the impeller assembly 418. The location of the housing bearing 432 may deviate approximately 0.050 inches from the center of mass of the impeller assembly 418 based on practical considerations for part assembly, but is optimized when located longitudinally as close as possible to the center of mass of the impeller assembly 418. In other embodiments, the housing bearing 432 may not be aligned with the center of mass of the impeller assembly 418 or the location of the housing bearing 432 may deviate by greater distances from the center of mass of the impeller assembly 418, depending on the size and configuration of the housing bearing 432.

The bearing assembly 430 is used to control the forces associated with impeller assembly 418. In part, the bearing assembly 430 utilizes the magnetic force of the driven magnet 412 to control the axial load of the impeller assembly 418. Specifically, the axial attraction between the magnetic field source 404 and the driven magnet 412 are greater than thrust from the impeller assembly 418 pushing the impeller assembly 418 in the distal direction and thus prevents axial movement of the impeller assembly 418 in the distal direction. The thrust bearing 434 provides axial control by countering the axial magnetic force attraction from magnetic field source 404 and the driven magnet 412. The housing bearing 432 provides radial control of the impeller assembly 418.

With continued reference to FIG. 4, the impeller assembly housing 420 includes a channel 444 located on the proximal side of at least one of the plurality of outlet apertures 424. The channel 444 is configured for receiving a guidewire (not shown) that passes from within impeller housing 420 to outside impeller housing 420 via one of the plurality of outlet apertures 424. In some embodiments, the channel 444 may extend the entire length of the housing bearing 432. The channel 444 provides a surface for a guidewire to gradually transition from within impeller housing 420 to outside impeller housing 420, decreasing the chances for damaging the guidewire due to contact with the impeller housing 420 and decreasing the angle of the guidewire during the transition within the impeller housing 420 to outside the impeller housing 420. The stationary surface of the housing bearing 432 may allow for features like an adhesive fillet or soft polymer component to prevent the proximal edge of the outlet aperture 424 from having a metal edge which can damage the guidewire.

One advantage of positioning the bearing assembly 430 as shown in FIG. 4 is that no bearing is necessarily required between the driven magnet 412 and the magnetic field source 404. Consequently, the driven magnet 412 and the magnetic field source 404 may be positioned closer together than in designs where a bearing assembly is located at the proximal end of the impeller assembly. For example, in the illustrated embodiment, the distance between the driven magnet 412 and the magnetic field source 404 could be as little as 0.012 inches, preferably less than 0.020 inches, and more preferably less than 0.030 inches. By reducing the distance between the driven magnet 412 and the magnetic field source 404, less magnetic flux is lost to space, which increases the magnetic torque transfer. The improved capture of magnetic flux from the magnetic field source 404 by reducing the spatial distance from the magnetic field source 404 to the driven magnet 412 enables more torque for higher flow rate designs, use of more corrosion resistant magnets, and smaller form factors. Reduction of the distance between the driven magnet 412 and the magnetic field source 404 may increase magnetic torque transferred to the driven magnet 412 by 100%.

Another advantage of the device 400 is that the impeller assembly 418 may be controlled both longitudinally and radially with only one bearing assembly. As noted above, previous blood pumps have been known to incorporate at least two bearing assemblies, often positioning one bearing assembly near the proximal end of the impeller assembly and another bearing assembly near the distal end of the impeller assembly, to control the longitudinal and radial motion of the impeller assembly. In contrast, the device 400 lacks a bearing assembly at a distal end 444 of the impeller 406, thereby reducing the number of blood-contacting bearing assemblies and preferably reducing the number of bearings down to two. As also noted above, reducing the number of surfaces or structures exposed to blood reduces the risks of hemolysis and thrombosis, and may also reduce the overall rigid length of the blood pump.

In some embodiments, a method of assembling the device 400 may include the following actions. Initially, the shaft is positioned in the impeller 406, and the thrust bearing 434 is positioned on the shaft 428 and against the proximal side 436 of the impeller 406. The thrust bearing 434 is then secured to the shaft 428 or impeller 406 (for example, via adhesive, press fit, mechanical coupling, sintering, welding or any method known by a person of ordinary skill in the art). The housing bearing 432 is then positioned on the shaft 428 proximally from the thrust bearing 434, and the driven magnet 412 is positioned on the shaft 428 proximally from the housing bearing 432. Next, the driven magnet 412 is secured to the shaft 428 (for example, via adhesive, press fit, mechanical coupling, sintering, welding or any method known by a person of ordinary skill in the art). The impeller assembly 418 and the bearing assembly 430 are then positioned in the impeller assembly housing 420, and the housing bearing 432 is secured to the impeller assembly housing 420 (for example, via adhesive, press fit, mechanical coupling, sintering, welding or any method known by a person of ordinary skill in the art).

The illustrative circulatory support device 400 shown in FIG. 4 is not intended to suggest any limitation as to the scope of use or functionality of embodiments of the present disclosure. The illustrative circulatory support device 400 also should not be interpreted as having any dependency or requirement related to any single component or combination of components illustrated therein. Additionally, various components depicted in FIG. 4 may be, in embodiments, integrated with various ones of the other components depicted therein (and/or components not illustrated), all of which are considered to be within the ambit of the present disclosure.

Figure 5:
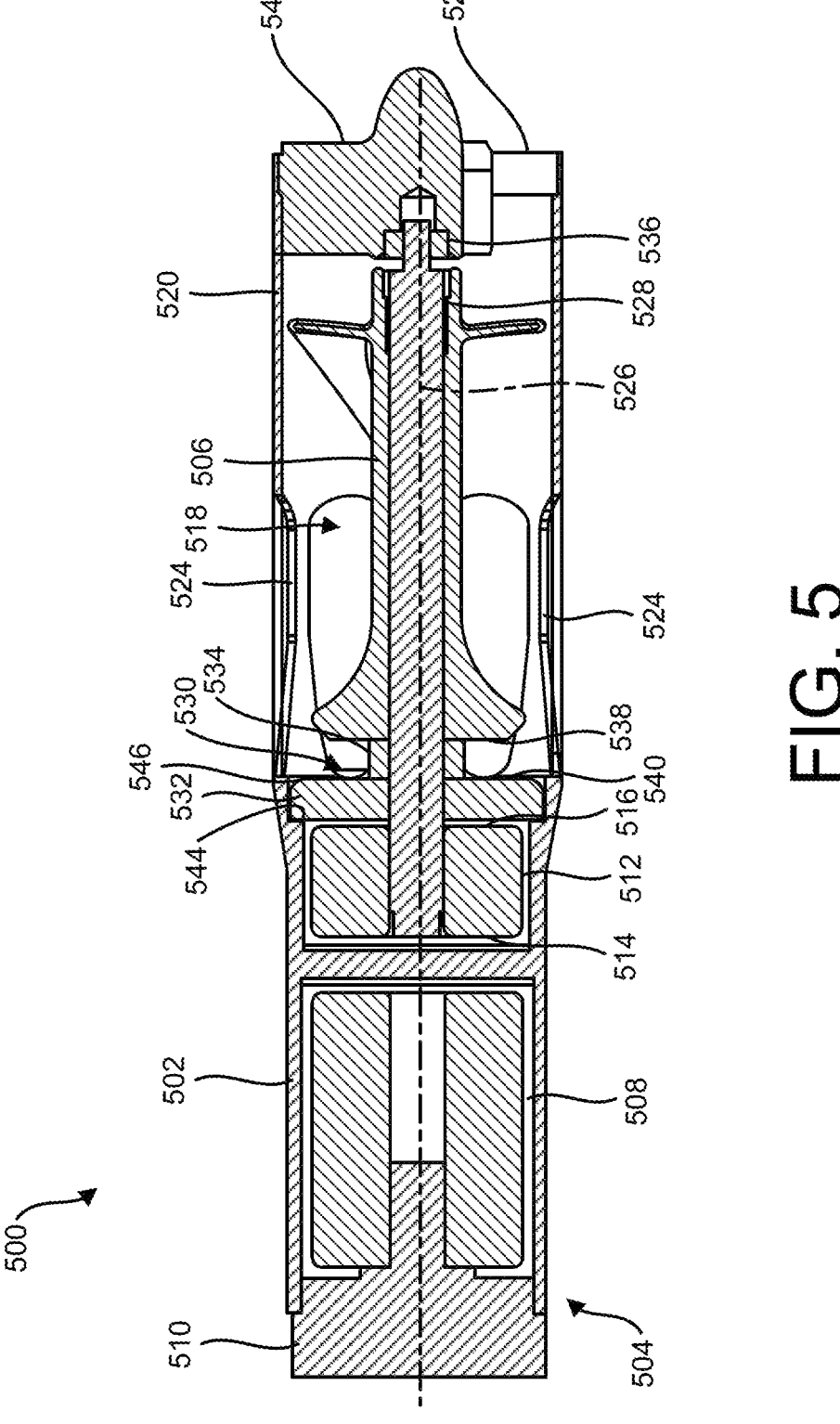
FIG. 5 depicts a cross-sectional view of yet another embodiment of an illustrative percutaneous mechanical circulatory support device, in accordance with embodiments of the subject matter disclosed herein.

FIG. 5 depicts a cross-sectional side view of an illustrative percutaneous mechanical circulatory support device 500 (also referred to herein, interchangeably, as a "blood pump"), in accordance with embodiments of the subject matter disclosed herein. According to embodiments, the blood pump 500, and/or any number of various components thereof, may be the same as, or similar to, corresponding components of the circulatory support device 100 depicted in FIGS. 1A and 1B, the same as, or similar to, corresponding components of the circulatory support device 200 depicted in FIGS. 2A and 2B, or the same as, or similar to, corresponding components of the circulatory support device 400 depicted in FIG. 4.

As shown in FIG. 5, the blood pump 500 includes a magnetic driving housing 502, which contains a magnetic field source 504 configured to produce a varying magnetic field to drive rotation of an impeller 506 to provide a flow of blood through the blood pump 500. In the embodiment shown in FIG. 5, the magnetic field source 504 includes a permanent driving magnet 508, rotated by a motor 510 and configured to cause rotation of a permanent driven magnet 512 coupled to the impeller 506 to provide a flow of blood through the blood pump 500. As shown, the driven magnet 512 includes a proximal side 514 and a distal side 516. In alternative embodiments, as described above but not shown here, the magnetic field source 504 may include a set of electromagnetic coils or a stator and motor for generating a magnetic field to cause rotation a permanent driven magnet coupled to an impeller to provide a flow of blood through blood pump.

A controller (not shown) is operably coupled to the motor 510 and is configured to control the motor 510. The controller may be disposed within the motor 510 in some embodiments, or in other embodiments, may be disposed outside the motor 510 (e.g., in a catheter handle, independent housing, etc.). In some embodiments, the controller may include multiple components, one or more of which may be disposed within the motor 510. According to some embodiments, the controller coupled to the motor 510 may be similar to the controller coupled to the motor 102 described in connection with FIG. 1A.

As shown in FIG. 5, an impeller assembly 518 is disposed within an impeller assembly housing 520, which includes an inlet aperture 522 and a plurality of outlet apertures 524 defined therein. A longitudinal axis 526 extends through the impeller assembly 518. According to some embodiments and as illustrated, the magnetic driving housing 502 and the impeller assembly housing 520 may be integrated with one another. In other embodiments, the magnetic driving housing 502 and the impeller assembly housing 520 may be separate components configured to be coupled together, either removably or permanently. The impeller assembly 518 includes the impeller 506 and the driven magnet 512. The driven magnet 512 and the impeller 506 may be coupled in a variety of ways, including through the use of adhesive, mechanical coupling, or interference fit. The driven magnet 512 may be any type of magnetic rotor capable of being driven by the magnetic field source 504. As a magnetic field is applied to the driven magnet 512 by the magnetic field source 504, the driven magnet 512 rotates, causing the impeller 506 to rotate. Rotation of the impeller 506 causes blood flow through the blood pump 500.

As shown in FIG. 5, the driven magnet 512 and the impeller 506 may be coupled via a drive shaft 528 coupled to the impeller 506 and configured to rotate with the impeller 506. The driven magnet 512 may be coupled to the drive shaft 528 and the impeller 506 in a variety of ways, including through the use of adhesive, mechanical coupling, or interference fit. The drive shaft 528 may be at least partially disposed within the impeller 506. The drive shaft 528 may also be at least partially surrounded by the driven magnet 512. The drive shaft 528 may be made of any number of different rigid materials such as, for example, steel, titanium alloys, cobalt chromium alloys, nitinol, high-strength ceramics, and/or the like.

As shown in FIG. 5, the impeller assembly 518 is coupled to and retained within the impeller assembly housing 520 by a proximal bearing assembly 530. According to some embodiments, the proximal bearing assembly 530 may be located near the distal side 516 of the driven magnet 512. According to some embodiments, the proximal bearing assembly 530 may include different types of bearings. The proximal bearing assembly 530 may also include lubrication, while in other embodiments, the proximal bearing assembly 530 may be free of lubrication. As shown in FIG. 5, the proximal bearing assembly 530 includes a first bearing 532, which may also be referred to as a housing bearing, and a second bearing 534, which may also be referred to as a thrust bearing. A third bearing 536, which may also be referred to as a distal bearing, is also included the impeller assembly 520 and coupled to the impeller assembly 518. The thrust bearing 534 contacts a proximal side 538 of the impeller 506 and a distal side 540 of the housing bearing 532. The distal bearing 536 is positioned distally relative to the impeller 506 and contacts a distal support 542, which in turn contacts the impeller assembly housing 520. The proximal bearing assembly 530 and the distal bearing 536 may be made of one or more materials resistant to corrosion, such as silicone nitride, ceramics, sapphire, Vespel, torlon, PTFE, or any other material resistant to corrosion known by a person of ordinary skill in the art.

With continued reference to FIG. 5, the housing bearing 532 contacts the impeller assembly housing 520. More specifically, the impeller assembly housing 520 includes a recess or pocket 544 that receives the housing bearing 532. The housing bearing 532 rotatably carries the shaft 528. In some embodiments, the housing bearing 532 reduces or minimizes an amount of blood that contacts the driven magnet 512, which may facilitate reduced hemolysis. In particular, the housing bearing 532 may include a rounded outer corner 546 that reduces or minimizes hemolysis of blood flowing through the device 500. In some embodiments, by having the driven magnet 512 behind the housing bearing 532, the housing bearing 532 reduces or minimizes the amount of blood that contacts the driven magnet 512, which may facilitate reduced hemolysis. In some embodiments, the housing bearing 532 may be positioned to be longitudinally near the center of mass of the impeller assembly 518, as described previously. The device 500 may be optimized when the housing bearing 532 is aligned with the center of mass of the impeller assembly 518. In other embodiments, the housing bearing 532 may not be aligned with the center of mass of the impeller assembly 518, depending on the size and configuration of the housing bearing 532.

In some embodiments and as illustrated, the driven magnet 512 and the magnetic field source 504 are positioned closer together than in designs where a bearing assembly is located at the proximal end of the impeller assembly. For example, in the illustrated embodiment, the distance between the driven magnet 512 and the magnetic field source 504 could be as little as 0.012 inches, preferably less than 0.020 inches, and more preferably less than 0.030 inches. By reducing the distance between the driven magnet

512 and the magnetic field source 504, less magnetic flux is lost to space, which increases the magnetic torque transfer. The improved capture of magnetic flux from the magnetic field source 504 by reducing the spatial distance from the magnetic field source 504 to the driven magnet 512 enables more torque for higher flow rate designs, use of more corrosion resistant magnets, and smaller form factors. Reduction of the distance between the driven magnet 512 and the magnetic field source 504 may increase magnetic torque transferred to the driven magnet 512 by 100%.

In some embodiments, a method of assembling the device 500 can be similar to the method of assembly of device 400 described above. In addition, the distal bearing 536 and the distal support 542 may be secured to each other and/or the impeller assembly housing 520 (for example, via adhesive, press fit, mechanical coupling, sintering, welding or any method known by a person of ordinary skill in the art) before or after securing the housing bearing 532 and the impeller assembly 518 to the impeller assembly housing 520.

The illustrative circulatory support device 500 shown in FIG. 5 is not intended to suggest any limitation as to the scope of use or functionality of embodiments of the present disclosure. The illustrative circulatory support device 500 also should not be interpreted as having any dependency or requirement related to any single component or combination of components illustrated therein. Additionally, various components depicted in FIG. 5 may be, in embodiments, integrated with various ones of the other components depicted therein (and/or components not illustrated), all of which are considered to be within the ambit of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A blood pump, comprising:
   an impeller assembly housing;
   a magnetic field source coupled to the impeller assembly housing;
   an impeller assembly within the impeller assembly housing and including a longitudinal axis, an impeller, and a driven magnet, the driven magnet being longitudinally offset and distally disposed relative to the magnetic field source, the driven magnet being rotatable and longitudinally controlled by the magnetic field source, and the driven magnet comprising a distal side, the distal side facing the impeller; and
   a bearing assembly within and in contact with the impeller assembly housing and near the distal side of the driven magnet, wherein the bearing assembly is aligned longitudinally with a center of mass of the impeller assembly;
   wherein the impeller assembly further includes a shaft extending through the impeller and the driven magnet along the longitudinal axis.

2. The blood pump of claim 1, wherein the bearing assembly comprises:
   a first bearing that contacts the impeller assembly housing; and a second bearing that contacts the first bearing and the impeller.

3. The blood pump of claim 1, wherein the shaft is coupled to and rotatable with the impeller.

4. A blood pump, comprising:

an impeller assembly housing;

a magnetic field source coupled to the impeller assembly housing;

an impeller assembly within the impeller assembly housing and including a longitudinal axis, an impeller, and a driven magnet, the driven magnet being longitudinally offset and distally disposed relative to the magnetic field source, the driven magnet being rotatable by the magnetic field source; and a bearing assembly within and in contact with the impeller assembly housing and coupled to the impeller assembly, wherein no portion of the bearing assembly is located between the driven magnet and the magnetic field source, wherein at least a part of the bearing assembly is secured directly to the driven magnet.

5. The blood pump of claim 4, wherein the impeller assembly further includes a shaft.

6. The blood pump of claim 5, wherein the bearing assembly contacts the driven magnet and the impeller assembly housing.

7. The blood pump of claim 5, wherein the shaft is coupled to and rotatable with the impeller.

8. The blood pump of claim 4, wherein the impeller assembly housing includes a recess that receives the bearing assembly.

9. The blood pump of claim 4, wherein the impeller assembly has a center of mass and the bearing assembly is aligned longitudinally with the center of mass of the impeller assembly.

10. The blood pump of claim 4, wherein the impeller assembly housing contains no bearing assembly located at a distal end of the impeller.

\* \* \* \* \*